United States Patent [19]

Dukes

[11] Patent Number: 5,183,814
[45] Date of Patent: Feb. 2, 1993

[54] SELECTIVE OESTROGEN THERAPY FOR PERIMENOPAUSAL OR POSTMENOPAUSAL CONDITIONS

[75] Inventor: Michael Dukes, Wilmslow, United Kingdom

[73] Assignee: Imperial Chemical Industries PLC, London, England

[21] Appl. No.: 362,043

[22] Filed: Jun. 6, 1989

[30] Foreign Application Priority Data

Jun. 6, 1988 [GB] United Kingdom ............... 8813353

[51] Int. Cl.⁵ ............... A61K 31/56; A61K 31/165; A61K 31/10
[52] U.S. Cl. .................. 514/171; 514/170; 514/182; 514/622; 514/708; 514/709; 514/710; 514/712; 514/713
[58] Field of Search ............... 514/170, 171, 182, 622, 514/708, 709, 710, 712, 713

[56] References Cited

U.S. PATENT DOCUMENTS

| | | | |
|---|---|---|---|
| 4,659,516 | 4/1987 | Bowler et al. | 260/397.5 |
| 4,732,912 | 3/1988 | Pilgrim et al. | 514/510 |
| 4,826,831 | 5/1989 | Plunkett et al. | 514/170 |
| 4,894,373 | 1/1990 | Young | 514/239.2 |

OTHER PUBLICATIONS

Volker et al, Maturitas, 10:157–159 (1988).
Ottosson et al, Gynecol. obstet. Invest., 18:140–146; 296–302 (1984).
Chemical Abstracts, vol. 109, No. 3, Jul. 18, 1988, p. 73, Abstract No. 17199p.

Primary Examiner—Frederick E. Waddell
Assistant Examiner—Raymond J. Henley, III
Attorney, Agent, or Firm—Cushman, Darby & Cushman

[57] ABSTRACT

The invention relates to a therapeutic product comprising an oestrogen and a pure antioestrogen for simultaneous, sequential or separate use in selective oestrogen therapy of perimenopausal or postmenopausal conditions; to a process for the manufacture of said product and to a pharmaceutical composition containing said product. The invention also relates to a pharmaceutical composition comprising an oestrogen and a pure antioestrogen and to a process for the manufacture of said composition.

4 Claims, No Drawings

SELECTIVE OESTROGEN THERAPY FOR PERIMENOPAUSAL OR POSTMENOPAUSAL CONDITIONS

This invention relates to a therapeutic product for use in a new method of medical treatment and, more particularly, it relates to a product comprising an oestrogen and a pure antioestrogen for use in a new method for the treatment or prophylaxis of perimenopausal or postmenopausal conditions, particularly perimenopausal or postmenopausal osteoporosis. The invention also relates to a pharmaceutical composition comprising an oestrogen and a pure antioestrogen and to the use thereof in the manufacture of a new medicament for use in the treatment or prophylaxis of perimenopausal or postmenopausal conditions.

When a female animal, particularly a human female, enters the perimenopausal stage the animal's ovaries begin to secrete less of the female sex hormones, particularly oestradiol. Symptoms in women at this stage include the following: vasomotor disturbances (hot flushes), urogenital atrophy (particularly affecting the vagina and distal urethra), psychosomatic complaints, changes in lipid metabolism and osteoporosis. The rate of decline of ovarian function and the severity of the above-mentioned symptoms are highly variable between individual women but in a substantial number of individuals the symptoms are sufficiently severe that treatment is required. Oestrogen replacement therapy has been used in women and it is generally recognised to be effective in combatting the typical perimenopausal and post-menopausal symptoms (*British Medical Journal*, 1987, 295, 914; *American Journal of Obstet. and Gynecol.*, 1987, 156, 1298 and 1347). However oestrogen replacement therapy can also cause uterine hyperplasia, irregular vaginal menstruation and, in a small proportion of women, endometrial cancer (*American Journal of Obstet. and Gynecol.*, 1987, 156, 1313).

To combat the continuous unopposed stimulation of oestrogen-responsive tissues an oestrogen and a progestogen are normally co-administered for part of each treatment period thereby causing regular vaginal menstruation. (*American Journal of Obstet. and Gynecol.*, 1987, 156, 1304). However the continuation of menstrual periods is unattractive to many postmenopausal women and, in addition, progestogens can cause side effects, for example oedema, premenstrual irritability and breast tenderness.

Alternative therapies are therefore required.

It has recently been shown that compounds demonstrating a mixture of oestrogenic and antioestrogenic properties in warm-blooded animals, including humans, may be of use in the treatment of postmenopausal conditions (European Patent Specification No. 0178862). Particular compounds stated to have such activity include clomiphene and tamoxifen. Comprehensive reviews of the clinical usage of these compounds are available. for example a review of clomiphene by Clark et al. in *Pharmacology and Therapeutics*, 1982, Volume 15, pages 467 to 519, and a review of tamoxifen by Furr et al. in *Pharmacology and Therapeutics*, 1984, Volume 25, pages 127-205.

It has also recently been shown that a treatment regime comprising the dosing of a small amount of an oestrogen, for example oestrone sulphate or natural conjugated oestrogens, followed by the dosing of an antioestrogen, for example tamoxifen or clomiphene led to the partial inhibition of the maximum oestrogen-induced stimulation of uterine endometrial tissue (A. Kauppila et al., *Gynecol. obstet. Invest.*, 1988, 25, 58 and *Arch. Gynecol.*, 1983, 234, 49).

It has now been found that administration of an oestrogen and a pure antioestrogen, whether simultaneously, sequentially or separately, results in the oestrogen being selectively effective in some oestrogen-responsive tissues, for example bone, and being selectively opposed in other oestrogen-responsive tissues, for example the endometrium of the uterus, and this is the basis of the present invention.

A pure antioestrogen is a compound which possesses antioestrogenic activity and no oestrogenic activity. This may be demonstrated in rats by the effect of the compound in antagonising the increase in weight of the uterus of an immature female rat produced by administering oestradiol benzoate to said rat. Thus, when each of a pure antioestrogen and oestradiol benzoate are administered for 3 days to such a rat, a smaller increase in uterine weight is produced than the substantial increase which would be produced by the administration of oestradiol benzoate alone. Unlike the known antioestrogens tamoxifen and clomiphene, when a pure antioestrogen is administered alone to a rat no increase in uterine weight whatsoever is observed.

It is disclosed in European Patent Specification No. 138504 that certain preferred steroidal antioestrogens are pure antioestrogens. It is also disclosed in European Patent No. 124369 that certain preferred non-steroidal antioestrogens are pure antioestrogens.

According to the present invention there is provided a product comprising an oestrogen and a pure antioestrogen for simultaneous, sequential or separate use in selective oestrogen therapy of perimenopausal or postmenopausal conditions.

In a particular product of the invention the oestrogen component of a product of the invention is oestradiol, ethinyloestradiol, oestriol, oestrone, natural conjugated oestrogens, piperazine oestrone sulphate, mestranol, chlorotrianisene, dienoestrol, stilboestrol or hexoestrol or a pharmaceutically-acceptable ester thereof.

A pharmaceutically-acceptable ester of the oestrogen component of a product of the invention is, for example, an alkyl or aryl ester each of up to 12 carbon atoms. It will be appreciated that an ester of a steroidal oestrogen may be formed at the 3-position, the 17-position or at both of these positions. It will also be appreciated that an ester may be formed at one or both of the phenolic groups in some non-steroidal oestrogens, for example stilboestrol and hexoestrol. A suitable alkyl ester of up to 12 carbon atoms is, for example, an acetate, propionate, butyrate, valerate, hexanoate, heptanoate, octanoate, cyclopentylpropionate, nonanoate, decanoate, undecanoate or dodecanoate. A suitable aryl ester of up to 12 carbon atoms is, for example, a benzoate, toluate or naphthoate. A preferred pharmaceutically-acceptable ester of the oestrogen component of a product of the invention includes, for example, oestroadiol benzoate, oestradiol cyclopentylpropionate, oestradiol dipropionate, oestradiol heptanoate, oestradiol undecanoate, oestradiol valerate and stilboestrol dipropionate.

In a further particular product of the invention the pure antioestrogen is

N-n-butyl-N-methyl-, N-1H,1H-heptafluorobutyl-N-methyl-or N,N-(3-methylpentamethylene)-11-(3,17$\beta$-dihydroxyoestra-1,3,5(10)trien-7$\alpha$-yl)undecanamide;

N-n-butyl- or N-1H,1H-heptafluorobutyl-3-p-[4-(3,17β-dihydroxyoestra-1,3,5(10)-triene-7α-yl)butyl]-phenylpropionamide;

7α-(10-p-chlorophenylthiodecyl)-, 7α-(10-p-chlorophenylsulphinyldecyl)-, 7α-[9-(4,4,5,5,5-pentafluoropentylsulphinyl)nonyl]-, 7α-[10-(4,4,4-trifluorobutylsulphinyl)decyl]-or 7α-[10-(p-chlorobenzylsulphinyl)decyl]-oestra-1,3,5(10)triene-3,17β-diol; or 7α-(9-n-heptylsulphinylnonyl)oestra-1,3,5(10)-triene-3,17β-diol.

In a further particular product of the invention the pure antioestrogen is a compound of the formula:

NU—A—X—R¹ wherein NU is 6-hydroxy-2-p-hydroxyphenylnapth-1-yl and A is —(CH$_2$)$_{10}$—, —(CH$_2$)$_{11}$— or —(CH$_2$)$_5$-(1,4-phenylene)-(CH$_2$)$_2$—;

or NU is 1,2,3,4-tetrahydro-6-hydroxy-2-p-hydroxyphenylnaphth-1-yl (either the 1RS,2RS or 1RS,2SR isomer), or 1,2,3,4-tetrahydro-6-hydroxy-2-p-hydroxyphenyl-2-methylnapth-1-yl (either the 1RS,2RS or 1RS,2SR isomer), and A is —(CH$_2$)$_{10}$—, —(CH$_2$)$_{11}$— or —(CH$_2$)$_4$-(1,4-phenylene)-(CH$_2$)$_2$—;

or NU is (1RS,2RS)-5-hydroxy-2-p-hydroxyphenylindan-1-yl or (1RS,2RS)-5-hydroxy-2-p-hydroxyphenyl-2-methylindan-1-yl and A is —(CH$_2$)$_{10}$—, —(CH$_2$)$_{11}$— or —(CH$_2$)$_4$-(1,4-phenylene)-(CH$_2$)$_2$—; and wherein XR¹ is —CONR¹R² wherein R² is hydrogen or methyl and R¹ is n-butyl, 1H,1H-heptafluorobutyl, n-pentyl or n-hexyl, or XR¹ is —SR¹, —SOR¹ or —SO$_2$R¹ wherein R¹ is n-pentyl, n-hexyl, 4,4,5,5,5-pentafluoropentyl or 1H,1H,2H,2H,3H,3H-heptafluorohexyl.

In a further particular product of the invention the pure antioestrogen is

N-n-butyl-, N-n-butyl-N-methyl-, N-n-pentyl, N-(1H,1H-heptafluorobutyl)-or N-(1H,1H-heptafluorobutyl)-N-methyl-3-p-[5-(6-hydroxy-2-p-hydroxyphenylnaphth-1-yl)pentyl]phenylpropionamide;

N-methyl-N-(1H,1H-heptafluorobutyl)-p-[4-[(1RS,2RS)-6-hydroxy-2-p-hydroxphenyl-2-methyl-1,2,3,4-tetrahydronaphth-1-yl]-butyl]phenylpropionamide; (1RS,2RS)-1-[4-[p-(2-n-hexylthioethyl)phenyl]-butyl]-2-p-hydroxyphenyl-1,2,3,4-tetrahydronaphth-6-ol or the corresponding 4,4,5,5,5-pentafluoropentylthio derivative, or the corresponding hexylsulphinyl, hexylsulphonyl or pentafluoropentylsulphinyl derivatives; 2-p-hydroxyphenyl-1-[5-[p-(2-n-hexylthioethyl)-phenyl]pentyl]naphth-6-ol or the corresponding hexylsulphinyl derivative; or (1RS,2RS)-1-[4[p-(2-n-hexylthioethyl)phentyl]butyl]-2-p-hydroxyphenyl-2-methyl-1,2,3,4-tetrahydronaphth-6-ol or the corresponding 4,4,5,5,5-pentafluoropentylthio derivative, or the corresponding hexylsulphinyl or pentafluoropentylsulphinyl derivative, or the corresponding (1RS,2SR) isomers of both the hexylthio and hexylsulphinyl derivatives.

A preferred product of the invention comprises an oestrogen and a pure antioestrogen for use as stated above wherein the oestrogen is oestradiol or ethinyloestradiol, or a pharmaceutically-acceptable ester thereof, and the pure antioestrogen is 7α-[9-(4,4,5,5,5-pentafluoropentylsulphinyl)nonyl]oestra-1,3,5(10)-triene-3,17β-diol or (1RS,2RS)-2-p-hydroxyphenyl-2-methyl-1-[9-(4,4,5,5,5-pentafluoropentylsulphinyl)nonyl]-1,2,3,4-tetrahydronaphth-6-ol.

A particularly preferred product of the invention comprises an oestrogen and a pure antioestrogen for use as stated above wherein the oestrogen is oestradiol, oestradiol benzoate, oestradiol valerate or oestradiol undecanoate and the pure antioestrogen is 7α-[9-(4,4,5,5,5-pentafluoropentylsulphinyl)nonyl]oestra-1,3,5(10)-triene-3,17β-diol.

According to a further feature of the invention there is provided a process for the manufacture of a product comprising an oestrogen and a pure antioestrogen for simultaneous, sequential or separate use in selective oestrogen therapy of perimenopausal or postmenopausal conditions, which process comprises bringing together said oestrogen and said pure antioestrogen.

In a further feature of the invention there is provided a process for the manufacture of a product comprising an oestrogen and a pure antioestrogen for simultaneous use in selective oestrogen therapy of perimenopausal or postmenopausal conditions, which process comprises bringing into admixture said oestrogen and said pure antioestrogen.

A product of the invention may be administered to a warm-blooded animal, including a human, in the form of a pharmaceutical composition. Thus according to a further feature of the present invention there is provided a pharmaceutical composition which comprises the product of the invention together with a pharmaceutically-acceptable diluent or carrier.

As mentioned above a product of the invention is useful for selective oestrogen therapy of perimenopausal or postmenopausal conditions. It will be understood that there is no absolute requirement that the oestrogen and pure antioestrogen components of the product of the invention must be dosed simultaneously. Sequential or separate use of these components may also provide selective oestrogen therapy and such use is to be understood to fall within the definition of a product of the invention. Thus it will be appreciated that a pharmaceutical composition according to the present invention includes a composition comprising an oestrogen, a pure antioestrogen and a pharmaceutically-acceptable diluent or carrier. Such a composition conveniently provides the product of the invention for simultaneous use in selective oestrogen therapy of perimenopausal or postmenopausal conditions. A pharmaceutical composition according to the present invention also includes separate compositions comprising a first composition comprising an oestrogen and a pharmaceutically-acceptable diluent or carrier, and a second composition comprising a pure antioestrogen and a pharmaceutically-acceptable diluent or carrier. Such a composition conveniently provides the product of the invention for sequential or separate use in selective oestrogen therapy of perimenopausal or postmenopausal conditions.

The compositions of the invention may be in a form suitable for oral use (for example as tablets, capsules, aqueous or oily suspensions, emulsions or dispersible powders or granules), for topical use (for example as creams, ointments, gels, or aqueous or oily solutions or suspensions; for example for use within a transdermal patch), for parenteral administration (for example as a sterile aqueous or oily solution or suspension for intravenous, subcutaneous, intramuscular or intravascular dosing), or as a suppository for rectal dosing or as a pessary for vaginal dosing.

The compositions of the invention may be obtained by conventional procedures using conventional pharmaceutical excipients, well known in the art.

Suitable pharmaceutically acceptable excipients for a tablet formulation include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, castor oil, sesame oil or coconut oil) or in a mineral oil (such as liquid paraffin). The oily suspensions may also contain a thickening agent such as beeswax, hard paraffin or cetyl alcohol. Sweetening agents, such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

The pharmaceutical compositions of the invention may also be in the form of oil-in-water emulsions. The oily phase may be a vegetable oil, such as castor oil, soya bean oil or arachis oil, or a mineral oil, such as, for example, liquid paraffin or a mixture of any of these. Suitable emulsifying agents may be, for example, naturally-occurring gums such as gum acacia or gum tragacanth, naturally-occurring phosphatides such as lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

The pharmaceutical compositions may also be in the form of sterile injectable aqueous or oily suspensions, which may be formulated according to known procedures using one or more of the appropriate dispersing or wetting agents and suspending agents which have been mentioned above. A sterile injectable preparation may also be a sterile injectable solution or suspension in a non-toxic parenterally-acceptable diluent or solvent, for example a solution in 1,3-butanediol, in a vegetable oil (such as arachis oil, castor oil or coconut oil) or in a mineral oil (such as liquid paraffin).

Conveniently the subcutaneous or intramuscular injection of an aqueous suspension or an oily solution or suspension of a pharmaceutical composition of the invention provides a depot of the active ingredients at the injection site from which those ingredients may leach out over a period of time to provide the sustained release thereof.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

According to a further feature of the invention there is provided a process for the manufacture of a pharmaceutical composition as defined above which comprises bringing into admixture a product as defined above together with a pharmaceutically-acceptable diluent or carrier.

The invention also provides a method of selective oestrogen therapy of perimenopausal or postmenopausal conditions which comprises administering simultaneously, sequentially or separately to a warm-blooded animal an effective amount of a product as defined above. The invention also provides the use of a product as defined above for the manufacture of a new medicament for use simultaneously, sequentially or separately in selective oestrogen therapy of perimenopausal or postmenopausal conditions.

It will be appreciated that the definition of the product of the invention and the pharmaceutical composition of the invention includes only those products or compositions which are useful in a new method for the treatment or prophylaxis of perimenopausal or postmenopausal condition. Pharmaceutical compositions comprising an oestrogen and a pure antioestrogen, together with a pharmaceutically-acceptable diluent or carrier, are novel. In European Patent Sepcifications Nos. 138504 and 124369 it is disclosed that the antioestrogenic activity of the compounds disclosed therein may be demonstrated by the co-administration of a test compound and oestradiol benzoate to an immature female rat. Antioestrogenic activity is demonstrated by antagonism of the increase in weight of the uterus of the rat which is produced when oestradiol benzoate alone is administered to said rat. It is to be noted that, during those tests, the oestradiol benzoate was given by subcutaneous injection whereas the test compound was given separately either orally or subcutaneously.

According to a further aspect of the invention there is provided a pharmaceutical composition comprising an oestrogen and a pure antioestrogen together with a pharmaceutically-acceptable diluent or carrier.

The pharmaceutical compositions of this feature of the invention may be obtained by conventional procedures using conventional pharmaceutical excipients well known in the are such as, for example, those disclosed above.

This aspect of the invention also provides a process for the manufacture of a pharmaceutical composition as defined immediately above which comprises bringing into admixture an oestrogen and a pure antioestrogen together with a pharmaceutically-acceptable diluent or carrier.

This aspect of the invention also provides a method of selective oestrogen therapy of perimenopausal or postmenopausal conditions which comprises administering to a warm-blooded animal an effective amount of a pharmaceutical composition as defined immediately above. The invention also provides the use of a pharmaceutical composition as defined immediately above for the manufacture of a new medicament for use in selective oestrogen therapy of perimenopausal or postmenopausal conditions.

As stated above a product of the invention is of use in selective oestrogen therapy of perimenopausal or postmenopausal conditions. Selective oestrogen therapy may be demonstrated using the standard procedure set out below:

a) an in vivo assay measuring the antioestrogenic activity of a compound and any oestrogenic activity possessed by that compound. This may be demonstrated in rats by the effect of the compound in antagonising the increase in weight of the uterus of an immature female rat produced by administering oestradiol benzoate to said rat. Thus, when each of a pure antioestrogen and oestradiol benzoate are administered for 3 days to such a rat, a smaller increase in uterine weight is produced than the substantial increase which would be produced by the administration of oestradiol benzoate without the pure antioestrogen. Unlike the known antioestrogens tamoxifen and clomiphene, when a pure antioestrogen is administered alone to a rat no increase in uterine weight whatsoever is observed.

The oestrogenic activity of a compound may be demonstrated in rats by the effect of the compound when it is administered alone to said rat on the uterine weight of the animal.

b) An in vivo assay in mature rats measuring the antioestrogenic activity of a compound by the effect of the compound when dosed during a test period of 28 days in antagonising the protective effect on the animals' bone density of their endogenous oestrogens. The bone density of a group of ovariectomised rats in which endogenous oestrogen levels are much reduced serves as a control for the effect expected to be produced by a fully effective antioestrogen.

The antioestrogenic activity of the compound in mature rats can also be measured in the same assay by measuring the effect of the compound in antagonising the effect of the animals' endogenous oestrogens which serve to increase the weight of their uteri.

A comparison of the potencies of the antioestrogenic effects of a compound as measured by its effects on the animals' bone density and uterine weights allows the selectivity of the antioestrogenic effects of the compound to be measured.

Although the pharmacological properties of a product of the invention vary with the structures of the oestrogenic and antioestrogenic components and with the route of administration, in general a product of the invention comprises:

(i) an oestrogen which possesses oestrogenic activity in the above test (a) at doses in the range, for example, 0.002–2.0 mg/kg orally or in the range, for example, 0.0001–0.1 mg/kg subcutaneously;

(ii) a pure antioestrogen which possesses antioestrogenic activity in the above tests (a) and (b) at doses in the range, for example, in test (a): $ED_{50}$ 0.05–5 mg/kg orally or $ED_{50}$ 0.01–1.0 mg/kg subcutaneously; in test (b): antiuterotrophic effect: $ED_{50} < 20$ mg/kg/day orally, $<2$ mg/kg/day subcutaneously or intramuscularly and $<10$ mg/kg/injection when dosed as an intramuscular depot injection; reduction in bone density: $ED_{50} > 20$ mg/kg/day orally, $>5$ mg/kg/day subcutaneously or intramuscularly and $>10$ mg/kg/injection when dosed as an intramuscular depot injection.

A product of the invention is thereby seen to be surprisingly selective as the activity of the pure antioestrogen component is expressed to a high degree within uterine tissue but to a lesser degree on bone.

The size of the dose, for therapeutic or prophylatic purposes, of a product of the invention as defined above will naturally vary according to the nature and severity of the conditions presented, the age and menopausal state of the animal and the route of administration.

In general the minimum quantity of the oestrogenic component of a product of the invention as defined above will be chosen so as to provide a beneficial effect with regard to the nature and severity of the conditions presented. The quantity of the pure antioestrogenic component is then chosen to antagonise to a substantial degree the effect of the oestrogenic component on the uterine tissue. Methods of evaluating the condition of uterine tissue are well known to the man skilled in the art, for example, by examination of a specimen of endometrial tissue taken by, for example, suction or, for example, by way of a biopsy.

So far as the oestrogenic component of a product of the invention as defined above is concerned the size of the dose and routes of administration conventionally utilised in oestrogen replacement therapy may be used. Thus, for example, a tablet containing, for example, 0.5 to 2 mg of oestradiol, oestradiol benzoate, natural conjugated oestrogens or oestradiol valerate may be administered daily. Alternatively a tablet containing 10 to 100 μg of ethinyloestradiol may be administered daily. Alternatively the oestrogenic component may be administered by, for example, intramuscular injection utilising, for example, 1 to 10 mg of oestradiol benzoate dissolved in an oil such as ethyl oleate; for example, transdermal means utilising, for example, 10–100 μg of oestradiol contained within a transdermal patch; or, for example, vaginal application utilising, for example, daily application of 0.5 to 2 mg of natural conjugated oestrogens contained within 0.5 to 5 ml of a cream.

So far as the antioestrogenic component of a product of the invention as defined above is concerned the size of the dose is chosen such that the effect of the oestrogenic component on uterine tissue is antagonised to a substantial degree whereas the beneficial effect of the oestrogenic component on bone is substantially unopposed. Thus, for example, the antioestrogenic component may be formulated in like manner to the oestrogenic component, for example as a tablet, an oily solution suitable for intramuscular injection, within a transdermal patch, or within a cream suitable for vaginal application. The daily administration of one or more tablets containing conveniently 50 mg to 5 g, and preferably 50 mg to 500 mg, of a pure antioestrogen may be used. Preferably the pure antioestrogen may be administered by the periodic intramuscular injection of, for example, an aqueous suspension or an oily solution or suspension containing 50 mg to 5 g of the pure antioestrogen. Preferably an oily solution, for example a solution containing arachis or castor oil, an alcohol such as benzyl alcohol and 50 mg to 500 mg of the pure antioestrogen is employed. Such an injection provides a depot of the pure antioestrogen which thereafter leaches out from the injection site to provide a selective antioestrogenic effect for a period of, for example, one to six weeks.

As mentioned above a product of the invention is useful for selective oestrogen therapy of perimenopausal or postmenopausal conditions. As previously mentioned perimenopausal and postmenopausal conditions include, for example, vasomotor disturbances (hot flushes), urogenital atrophy (particularly affecting the vagina and the distal urethra), psychosomatic complaints, changes in the lipid metabolism and oesteoporosis. The selective antioestrogenic effect of the pure antioestrogenic component of a product of the invention, as demonstrated by a greater antioestrogenic effect on the uterus of a rat than on the bone of the rat, allows the beneficial effect of the oestrogenic component of the product of the invention to be selectively applied to the bone and prevents the detrimental effect of an unopposed oestrogenic effect on the uterus. The utero-selective effect of the pure antioestrogenic component of a product of the invention will allow the beneficial effect of the oestrogenic component of a product of the invention to be applied to other oestrogen-responsive tissues, for example those causing vasomotor disturbances, pyschosomatic complaints and changes in lipid metabolism.

The invention will now be illustrated in the following nonlimiting Examples.

EXAMPLE 1

Assay in Mature Rats of the Selective Antioestrogenic Activity of a Pure Antioestrogen The pure antioestrogen used was (1RS,2RS)-2-p-hydroxyphenyl-2-methyl-1-[9-(4,4,5,5,5-pentafluoropentylsulphinyl)nonyl]-1,2,3,4-tetrahydronaphth-6-ol.

The compound was given subcutaneously as a solution in arachis oil at doses of 2 mg/kg/day and 10 mg/kg/day to two groups of 5 mature rats for a total of 28 days. Further groups of 5 mature rats served as an untreated control group. A further group of 5 mature rats was ovariectomised to serve as another control group. At the end of the treatment period the weights of the uteri of the test and control groups of rats were determined. In addition the femurs were dissected, weighed and their volumes were determined using Archimedes Principle. The femurs were then burned and the residual ash was weighed. From these data, gross femur density and bone mineral density were calculated as follows:

Gross Femur Density=Femur Weight/Femur Volume
Bone Mineral Density=Femur Ash Weight/Femur Volume The results shown below in Tables I and II demonstrate that at a dose of 2 mg/kg/day subcutaneously the test compound selectively inhibits the action of the animals' endogenous oestrogen on their uteri (90% inhibition of uterine weight) whereas there was no significant inhibition of either bone mineral density or of gross femur density.

TABLE I

| Treatment | Uterine Weight (mg) | Calculated Inhibition |
|---|---|---|
| Untreated Controls | 382 ± 34 | |
| Ovariectomised Controls | 111 ± 14 | |
| Test Compound at 2 mg/kg/day s.c. | 135 ± 8 | 91% |
| Untreated Controls | 369 ± 47 | |
| Ovariectomised Controls | 99 ± 5 | |
| Test Compound at 10 mg/kg/day s.c. | 125 ± 4 | 90% |

EXAMPLE 2

The experiment described in Example 1 was repeated except that the pure antioestrogen used was 7α-[9-(4,4,5,5,5-pentafluoropentylsulphinyl)nonyl]oestra-1,3,5(10)-triene-3,17β-diol. This compound was given at a series of doses as a daily intramuscular injection, the compound having been dissolved in a mixture of propylene glycol: ethanol: water: poloxamer 407. The formulation contained 25 mg of test compound, 100 mg of ethanol (96%), 100 mg of water, 20 mg of poloxamer 407 and sufficient propylene glycol to bring the solution to a volume of 1 ml.

The results shown below in Tables III and IV demonstrate that at all doses tested the compound selectively inhibits the action of the animals' endogenous oestrogen on their uteri whereas there was no significant inhibition of gross femur density.

TABLE III

| Treatment | Uterine Weight (mg) | Calculated Inhibition |
|---|---|---|
| Untreated Controls | 302 ± 36 | |
| Ovariectomised Controls | 70 ± 1.3 | |
| Test Compound (mg/kg) | | |
| 0.1 | 208 ± 17 | 41 |
| 0.3 | 174 ± 16 | 55 |
| 1 | 94 ± 9 | 90 |
| 3 | 103 ± 2 | 86 |

TABLE IV

| Treatment | Gross Femur Density (g/ml) | Calculated Inhibition |
|---|---|---|
| Untreated Controls | 1.523 ± 0.008 | |
| Ovariectomised Controls | 1.491 ± 0.006 | |
| Test Compound at (mg/kg) | | |
| 0.1 | 1.528 ± 0.005 | 0% |
| 0.3 | 1.528 ± 0.008 | 0% |
| 1 | 1.532 ± 0.005 | 0% |
| 3 | 1.533 ± 0.005 | 0% |

EXAMPLE 3

The pure antioestrogen used was 7α-[9-(4,4,5,5,5-pentafluoropentylsulphinyl)nonyl]oestra-1,3,5(10)-triene-3,17β-diol.

Each of a series of selected doses of this compound was dissolved in a mixture of castor oil and benzyl alcohol and given by intramuscular injection to a group of 5 mature rats. The formulation contained 50 mg of the test compound, 400 mg of benzyl alcohol and sufficient castor oil to bring the solution to a volume of 1 ml. In each case a second dose was administered two weeks after the first dose. Two weeks after the second dose the weights of the uteri of the test groups of rats were determined. In addition the femurs were dissected and analysed for Gross Femur Density as in Example 1.

A further group of rats, given two injections of castor oil separated by a two week period, served as an intact control group. A further group of rats was ovariectomised to serve as another control group.

The results shown below in Tables V and VI demonstrate that at all doses tested the compound selectively inhibits the action of the animals' endogenous oestrogen on their uteri whereas at the two higher test doses there was no significant inhibition of gross femur density.

TABLE V

| Treatment | Uterine Weight (mg) | Calculated Inhibition |
|---|---|---|
| Intact Controls | 318 ± 31 | |
| Ovariectomised Controls | 76 ± 4 | |
| Test Compound (mg/rat/dose) | | |
| 0.75 | 202 ± 23 | 48 |
| 1.25 | 180 ± 15 | 57 |
| 2.5 | 123 ± 12 | 81 |

TABLE VI

| Treatment | Gross Femur Density (g/ml) | Calculated Inhibition |
|---|---|---|
| Intact Controls | 1.584 ± 0.007 | |
| Ovariectomised Controls | 1.521 ± 0.005 | |
| Test Compound (mg/rat/dose) | | |
| 0.75 | 1.562 ± 0.004 | 35* |
| 1.25 | 1.576 ± 0.004 | 13* |
| 2.5 | 1.569 ± 0.007 | 23* |

*This level of inhibition was not statistically significant.

What we claim is:

1. A method of selective oestrogen therapy of perimenopausal or postmenopausal conditions which comprises administering to a warm-blooded animal an oestrogen and a pure antioestrogen, the oestrogen and pure antioestrogen being present in amounts such that the oestrogen is effective only in selected oestrogen-responsive tissues and is selectively opposed in other oestrogen-responsive tissues.

2. The method as claimed in claim 1 wherein the pure antioestrogen is
   N-n-butyl-N-methyl-, N-1H,1H-heptafluorobutyl-N-methyl-or N,N-(3-methylpentamethylene)-11-(3,17β-dihydroxyoestra-1,3,5(10)-trien-7α-yl)undecanamide;
   N-n-butyl- or N-1H,1H-heptafluorobutyl-3-p-[4-(3,17β-dihydroxyoestra-1,3,5(10)-trien-7α-yl)butyl]phenylpropionamide;
   7α-(10-p-chlorophenylthiodecyl)-, 7α-(10-p-chlorophenylsulphinyldecyl)-, 7α-[9-(4,4,5,5,5-pentafluoropentylsulphinyl)nonyl]-, 7α-[10-(4,4,4-trifluorobutylsulphinyl)decyl]- or 7α-[10-(p-chlorobenzylsulphinyl)decyl]-oestra-1,3-5(10)-triene-3,17β-diol; or 7α-(9-n-heptylsulphinylnonyl)oestra-1,3,5(10)-triene-3,17β-diol.

3. The method as claimed in claim 1 wherein the pure antioestrogen is a compound of the formula:

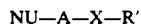

NU—A—X—R' wherein NU is 6-hydroxy-2-p-hydroxyphenylnaphth-1-yl and A is —(CH$_{12}$)$_{10}$—, —(CH$_2$)$_{11}$— or —(CH$_2$)$_5$-(1,4-phenylene)-(CH$_2$)$_2$—;
or NU is 1,2,3,4-tetrahydro-6-hydroxy-2-p-hydroxyphenylnaphth-1-yl (either 1RS,2RS or 1RS,2SR isomer), or 1,2,3,4-tetrahydro-6-hydroxy-2-p-hydroxyphenyl-2-methylnaphth-1-yl (either the 1RS,2RS or 1RS,2SR isomer), and A is —(CH$_2$)$_{10}$—, —(CH$_2$)$_{11}$— or —(CH$_2$)$_4$-(1,4-phenylene)-(CH$_2$)$_2$—;
or NU is (1RS,2RS)-5-hydroxy-2-p-hydroxyphenylindan-1-yl or (1RS,2RS)-5-hydroxy-2-p-hydroxyphenyl-2-methylindan-1-yl and A is —(CH$_2$)$_{10}$—, —(CH$_2$)$_{11}$— or —(CH$_2$)$_4$-(1,4-phenylene)-(CH$_2$)$_2$—;
and wherein XR$^1$ is —CONR$^1$R$^2$ wherein R$^2$ is hydrogen or methyl and R$^1$ is n-butyl, 1H,1H-heptafluorobutyl, n-pentyl or n-hexyl, or XR$^1$ is -SR$^1$, SOR$^1$ or -SO$_2$R$^1$ wherein R$^1$ is n-pentyl, n-hexyl, 4,4,5,5,5-pentafluoropentyl or 1H,1H,2H,2H,3H,3H,-heptafluorohexyl.

4. The method as claimed in claim 1, wherein the oestrogen is oestradiol, oestradiol benzoate, oestradiol valerate or oestradiol undecanoate and the pure antioestrogen is 7α-[9-(4,4,5,5,5-pentafluoropentylsulphinyl)-nonyl]oestra-1,3,5(10)triene-3,17β-diol.

* * * * *